United States Patent [19]
Naeger

[11] Patent Number: 5,661,142
[45] Date of Patent: Aug. 26, 1997

[54] ANTI-EMETIC COMPOSITION

[76] Inventor: David M. Naeger, 8 Gladiola Center, Newtown, Pa. 18940-4224

[21] Appl. No.: 634,083

[22] Filed: Apr. 17, 1996

[51] Int. Cl.$^6$ .................................................. A61K 31/56
[52] U.S. Cl. ...................... 514/178; 514/922; 514/872; 424/436
[58] Field of Search .................... 514/872, 922, 514/178; 424/436

[56] References Cited

U.S. PATENT DOCUMENTS

| | | |
|---|---|---|
| 4,007,273 | 2/1977 | Levinson et al. . |
| 4,436,741 | 3/1984 | Urquhart et al. ........................ 514/872 |
| 4,536,386 | 8/1985 | Keenan .................................. 514/872 |
| 4,624,965 | 11/1986 | Wenig . |
| 5,039,528 | 8/1991 | Olney . |
| 5,081,153 | 1/1992 | Pathak et al. . |
| 5,166,145 | 11/1992 | Jao et al. . |
| 5,310,561 | 5/1994 | Jao et al. . |
| 5,482,716 | 1/1996 | Tyers et al. . |

OTHER PUBLICATIONS

Roila, F. *Oncology*, (1993) 50:163–167.
Roila, F. *Am. J. Clin. Oncol.* (CCT), (1992) 15(2):112–114.
Warr, D. *Eur. J. Cancer* (1993) vol. 29A, No. 1:33–36.
Italian Group for Antiemetic Research *Journal of Clinical Oncology* (1993) vol. 11, No. 12:2396–2404.
Francom, M. *American Pharmacy* (1991) vol. NS31, No. 7, p. 7 (Letter to Editor).
Schmitt, R. et al. *ONF* (1990) vol. 17, No. 2:277 (Letter to Editor).
Markman, M. et al. *The New England Journal of Medicine* (1984) vol. 311, No. 9:549–552.
Harrington, R.A. et al. *Drugs* (1983) 25:451–494.
Markham, A. et al. *Drugs* (1993) 45(6):931–952.
Pitré, D. et al. *Analytical Profiles of Drug Substances* (1987) 16:327–361.
Kirk–Othmer *Pharmaceuticals* (1982) 17:272–310.
Adamski, P. Letter to Editor, *Oncology Nursing Forum*, vol. 18, No. 3, Apr. 1991, p. 604.

*Primary Examiner*—James H. Reamer
*Attorney, Agent, or Firm*—Lowe, Price, LeBlanc & Becker

[57] ABSTRACT

The invention relates to an anti-emetic composition that comprises dexamethasone (DEX), metoclopramide (MTC) and an antihistamine or an anticholinergic agent. In a particular embodiment, a composition containing DEX:MTC:diphenhydramine in a relative weight ratio of about 1:1:2.5, respectively, is found to be effective in providing relief from the discomfort caused by symptoms of both vomiting and nausea in all patients receiving the composition. Alternatively, an effective composition may contain DEX:MTC:scopolamine in a relative weight ratio of about 1:1:0.025, respectively. Other effective compositions and methods of their use are also disclosed.

23 Claims, No Drawings

ANTI-EMETIC COMPOSITION

FIELD OF THE INVENTION

The present invention relates to both a therapeutic composition comprising a combination of antiemetic drugs and to a method for treating emesis, including nausea.

BACKGROUND OF THE INVENTION

Nausea and vomiting can follow the administration of many drugs, particularly anticancer or chemotherapeutic agents. The symptoms also often accompany infectious and non-infectious gastrointestinal disorders.

The initial manifestations of the vomiting response often involves nausea, in which gastric tone is reduced, gastric peristalsis is reduced or absent and the tone of the duodenum and upper jejunum is increased, such that their contents reflux. Ultimately, the upper portion of the stomach relaxes while the pylorus constricts, and the coordinated contraction of the diaphragm and abdominal muscles leads to expulsion of gastric contents. Goodman and Gilman's *The Pharmacological Basis of Therapeutics*, 8th Edition, Pergamon Press, New York, pp. 925–928 (1990).

Many workers have studied the effects of various drugs in alleviating the symptoms of emesis. In the Goodman and Gilman text, the authors mention metoclopramide (MTC), a benzamide, as a dopaminergic antagonist with important antiemetic uses. Benzodiazepines, another class of drugs, can enhance the effectiveness of antiemetic regimens and are thought to be beneficial in the prevention of anticipatory emesis. Also, dexamethasone (DEX) and other glucocorticoids are said to have antiemetic effects and may improve the efficacy of antiemetic regimens in some cancer patients. The authors name six phenothiazine compounds, one butyrophenone, two benzamides including metoclopramide and two cannabinoids as agents used in the treatment of nausea.

Goodman and Gilman describe metoclopramide as being well tolerated in high intravenous dosages and being widely used to control emesis during cancer chemotherapy, especially when highly emetogenic agents, such as cisplatin or cyclophosphamide, are used. Metoclopramide has been combined with diphenhydramine (DPH). Regimens that are reportedly effective in countering vomiting induced by cisplatin or cyclophosphamide include those that utilize the intravenous administration of metoclopramide and dexamethasone in combination with lorazepam plus benztropine or droperidol plus diphenhydramine.

In an article by Markman et al., in the *New England Journal of Medicine*, Vol. 311, pp. 549–552 (1984), the authors compare the antiemetic effects of dexamethasone with prochlorperazine. It is concluded that there is less nausea and vomiting with dexamethasone than with the prochlorperazine. The authors also refer to two studies comparing the efficacy of high-dose dexamethasone and high-dose metoclopramide. The dexamethasone was said to be more effective than metoclopramide in controlling chemotherapy-induced nausea and vomiting and was preferred by the patients treated.

In a review of metoclopramide, in *Drugs* 25:451–494 (1983), at page 453, the authors assert that controlled trials have shown oral metoclopramide (30–40 mg daily) alleviates the symptoms of gastro-oesophageal reflux relative to placebo and increases lower oesophageal sphincter pressure.

In a more recent publication, Roila, in *Oncology* 50:163–167 (1993), discusses the results of administering ondansetron plus dexamethasone, compared to the standard metoclopramide combination. In the paper, a composition comprising metoclopramide (3 mg/kg), dexamethasone (20 mg) and diphenhydramine (50 mg), administered intravenously, is compared with a composition of ondansetron (0.15 mg/kg) and dexamethasone (20 mg), administered intravenously. The results, summarized in the last line of the abstract at page 163, advises that ondansetron plus dexamethasone is a more effective and better tolerated antiemetic regimen compared with metoclopramide plus dexamethasone and diphenhydramine for the prevention of acute cisplatin-induced emesis.

In the patented literature, such as U.S. Pat. No. 5,039,528, metoclopramide is described as the agent of choice for suppressing emesis associated with cancer therapy. However, the patentee notes, this agent exhibits effective antiemetic activity only when used at high doses. In U.S. Pat. No. 5,482,716, the patentees indicate that studies show the antiemetic properties of carbazolone(1,2,3,9-tetrahydro-9-methyl-3-[(2-methyl-1H-imidazol-1-yl)methyl]-4H-carbazol-4-one) are enhanced by administering the compound in conjunction with dexamethasone, a systemic anti-inflammatory corticosteroid that is known to have antiemetic properties. In U.S. Pat. No. 5,310,561, in Example 6, ondansetron is used with metoclopramide, haloperidol or droperidol, and dexamethasone, among others.

SUMMARY OF THE INVENTION

This invention relates to a method and a pharmaceutical composition for relieving nausea, emesis, or symptoms associated therewith. A pharmaceutical composition is provided for the relief of nausea, emesis, or symptoms associated therewith, which comprises a combination of dexamethasone (DEX), metoclopramide (MTC), an antihistamine (ATH) and an anticholinergic agent (ACA). The components DEX:MTC:ATH:ACA are present in a relative weight ratio of about 1:0–2:0–5:0–0.025, respectively, provided that (i) the DEX is not obtained from a commercially available DEX tablet, (ii) no less than three of the four components are present and (iii) the composition does not include the combination DEX:MTC:ATH, in which the ATH is diphenhydramine, in a relative weight ratio of 1:1:5.

In a particular embodiment of the invention, the composition comprises an effective amount of a combination comprising (a) finely divided dexamethasone or its salt, (b) metoclopramide and (c) diphenhydramine in a part by weight ratio of about 0.9 to 1.1 parts (a) to about 0.9 to 1.1 parts (b) to about 2.0 to 3.0 parts (c), preferably about 2.2 to 2.8 parts (c), more preferably about 2.4 to 2.6 parts (c). A preferred unit dosage form of the composition comprises about 10 mg each of said dexamethasone and metoclopramide and about 25 mg of diphenhydramine.

The composition may be in the form of a suppository or a solution for parenteral administration. Thus, a preferred weight ratio of the components (a):(b):(c) is about 1:1:2.5.

The composition of the invention can utilize a variety of dexamethasone derivatives, including esters thereof or salts thereof. In particular, the dexamethasone may be selected from the 21-(3,3-dimethylbutyrate), 21-phosphate, 21-phosphate dialkali metal salt, tetrahydrophthalate, 21-diethylaminoacetate, 21-isonicotinate, 21-(4-pyridinecarboxylate), 17,21-dipropionate, or 21-palmitate. Preferably, the dexamethasone is present as the phosphate salt, more preferably the dialkali or disodium phosphate salt and is most preferably the 21-phosphate disodium salt.

Each of the metoclopramide, diphenhydramine and scopolamine may be present in the form of a free base or an acid addition salt. For example, the metoclopramide may be used as the dihydrochloride monohydrate or the monohydrochloride monohydrate. Several forms of the diphenhydramine can be used, including but not limited to the hydrochloride, the ascorbate, or the p-sulfonamide benzoate derivative. Also, several derivatives and/or acid addition salts of scopolamine can be used including but not limited to the hydrobromide trihydrate, the hydrochloride, the methyl bromide, the methyl nitrate and the DL form, which may come as a monohydrate or dihydrate.

In addition, other antihistaminic agents can be used in the composition of the invention in place of diphenhydramine, including but not limited to antazoline, astemizole, azelastine, cetoxime, clemizole, clobenztropine, diphenazoline, mebhydroline, phenindamine, terfenadine, or tritoqualine. Also, other anticholinergic agents besides scopolamine can be used in the composition of the invention. Alternative ACAs include but are not limited to scopolamine N-oxide, adiphenine hydrochloride, benzetimide, benzilonium bromide, chlorphenoxamine, dicyclomine hydrochloride, eucatropine, flutropium bromide, isopropamide, methixene, phencarbamide, procyclidine, tropacine, or valethamate bromide.

Although the composition of the invention can come in a number of forms and can be administered in a number of ways, the preferred composition is in the form of a suppository. The suppository can be formulated by conventional means and may contain a number of non-active components, such as cocoa-butter, polyethylene glycol, or glycerogelatin base. In addition to the three principal effective agents in the composition, stabilizers, bulking agents, emulsifiers, pH buffers and other therapeutic agents, known in the art, may be incorporated into the composition.

In a particularly preferred embodiment of the invention, a finely divided, micronized form of dexamethasone is employed in the form of the dialkali metal phosphate salt. The particle sizes of the micronized dexamethasone can range in size from about 5 μm up to about 20 μm. It is important to note that the finely divided form of dexamethasone is preferably not obtained from a commercially available dexamethasone tablet that may contain a variety of non-active ingredients, including binders, which may apparently exert a detrimental effect on the efficacy of the composition to alleviate the symptoms of nausea and emesis. If the source of the dexamethasone is a commercial tablet, then the mixture obtained from the tablet should preferably be treated to provide the active ingredient relatively, preferably substantially, free of the non-active components. Methods of purification are well known to those of ordinary skill and may include dissolution of the mixture in a solvent and recrystallization, for example.

The composition is administered to a patient suffering from nausea, emesis or associated symptoms thereof. Once relief has been provided, the composition can be administered under a regimen to maintain a substantially symptom-free state. Generally, the dosage or frequency of administration of the composition of the invention to keep the patient essentially free of the complained of afflictions will be less than the dosage or frequency used in the initial phase of treatment. The dosage or frequency can be cut back until the ailments begin to manifest themselves once again. The dosage or frequency is then adjusted to just suppress the symptoms.

The composition of the invention can thus be provided as part of a chemotherapeutic regimen with the benefit that the patient is better able to withstand the discomfort associated with same. The composition can be administered twice to three times daily. Thereafter, the composition can be taken once a day or less for maintaining a symptom-free state.

Since oral administration is often impossible, the composition is most preferably used in the form of a suppository, which is inserted into a patient's rectum, vagina, or otherwise administered across a patient's mucosal membrane. Also, the composition may be made available in a form suitable for parenteral administration, e.g., intravenous, intraperitoneal or intramuscular.

The composition of the invention is useful for providing relief to a patient experiencing an emetogenic condition. The present composition is particularly efficacious for treating patients undergoing, about to undergo, or recovering from chemotherapy for a deadly disease, such as cancer. However, other conditions, such as vertigo, motion sickness, AIDS, food poisoning and other acute or chronic diseases and infections that cause nausea, emesis, or associated symptoms thereof, may be effectively treated by the administration of the composition disclosed herein. In particular, the composition of the invention finds exceptional beneficial use in patients who have either exhausted all other medical alternatives or are considered terminally ill. In these patients (no matter what the cause of their illness) the composition provides exceptional relief of unwanted symptoms of nausea, vomiting and the like.

Moreover, it may be desirable to administer the present composition in the form of a controlled release formulation whereby constant uniform relief is provided over a predetermined period of time. This release may be accomplished by formulating the composition in a conventional vehicle for parenteral administration or encapsulating the composition in liposomes in a suppository and administering said suppository to the patient. By this method, relief from the debilitating effects of chemotherapy, cancer, immune deficiency and other potentially emetogenic conditions, including terminal or near terminal illnesses, may be provided and effectively maintained.

It is also pointed out that a range of 0–2, 0–5, or 0–0.025, includes any amount within the recited range, as that amount relates to the amount of dexamethasone present in the composition, which dexamethasone amount is set to unity for the sake of comparison. In particular embodiments, the amounts of metoclopramide may be about 0 (i.e., substantially absent), 0.25, 0.5, 0.75, 1.0, 1.25, 1.5, 1.75, or 2.0 relative to dexamethasone. The antihistamine may thus be present, relative to dexamethasone, in about 0 (i.e., substantially absent), 0.25, 0.5, 0.75, 1.0, 1.25, 1.5, 1.75, 2.0, 2.25, 2.50, 2.75, 3.0, 3.25, 3.50, 3.75, 4.0, 4.25, 4.50, 4.75, or 5.0. The anticholinergic agent may also be present in about 0 (i.e., substantially absent), 0.005, 0.010, 0.015, 0.020, or 0.025 relative to dexamethasone.

EXAMPLES AND COMPARATIVE DATA

In the following comparative examples, variations in the prior art procedures and the differences in adverse events, such as diarrhea, extrapyramidal reactions, headache, hot flush, sedation, hiccup, sweating, etc. have not been included. The prior art and comparative examples are designated by a letter and the inventive composition is indicated by a number. In example A, disclosed by Roila, in *Oncology* 50:163–167 (1993), a composition comprising 20 mg DEX, 3 mg/kg MTC and 50 mg DIP is administered intravenously and obtains a 59% reported effectiveness. In Example B, Roila et al., in *Am. J. Clin. Oncol.* (CCT) 15:112–114 (1992), a composition similar to that in Example A is administered intravenously, with two 3 mg/kg doses of MTC being employed, for a reported effectiveness of 80.8% and 88.5% for vomiting and nausea, respectively, on the first day. Improved results of 96.2% for relief from vomiting and 88.5% protection from nausea is reported for the second day. In Example C, Warr et al., in *Eur. J. Cancer*, Vol. 29A, I, pp. 33-36 (1993), disclose a composition of 10 mg DEX, 2 mg/kg MTC and 10 mg DPH, which provides 58% protection against emesis. The composition of Example C is administered intravenously.

In a further article by Roila et al., in the *Journal of Clinical Oncology*, 11:2396-2404 (1993), the authors report the use of a composition comprising 20 mg DEX, 3 mg/kg MTC and 50 mg DPH, which is administered intravenously to obtain a 58.1% protection against vomiting with high-dose cisplatin and a 60.9% protection against low-dose cisplatin chemotherapy (Example D). In Example E, Francom, in *American Pharmacy*, Vol. NS 31, at page 7 (1991)/459, reports the administration of a suppository containing 10 mg DEX, 40 mg MTC and 25 mg DPH. No numerical results are given. Likewise, in Example F, Adamski, in *Oncol. Nursing Forum*, 18(3):604 (1991), reports the use of a suppository comprising 5 mg DEX, 20 mg MTC and 25 mg DPH without a numerical evaluation.

In Example G, Schmitt, in *ONF*, Vol. 17, page 277 (1990),. describes the preparation and use of a suppository comprising 5 mg DEX, 20 mg MTC and 25 mg DPH to obtain 80% effectiveness against nausea and vomiting.

In the inventor's own work, the use of a suppository comprising 5 mg DEX, 5 mg MTC and 25 mg DPH provides only a 40-50% rate of efficacy against either nausea or emesis. Subsequently, a composition having 10 mg DEX, 10 mg MTC and 25 mg DPH are compounded and administered as a suppository. The rate of effectiveness improves, but it is observed to be no higher than about 60-80%. In this first 10:10:25 composition, the dexamethasone is obtained from commercially available dexamethasone-containing tablets. The dexamethasone tablets are crushed using a mortar and pestle and this powder used to provide the desired content of dexamethasone.

In a surprising development, it has been discovered that when the source of the DEX is changed from the commercial dexamethasone tablet to a rawer, unfinished, finely divided form, the performance of the anti-emetic composition is significantly enhanced. Indeed, a composition comprising 10 mg of DEX in the form of a finely divided powder of dexamethasone dialkali phosphate salt, together with 10 mg MTC and 25 mg DPH, is found after prolonged extensive clinical use to be virtually 100% effective in providing relief against the discomfort caused by nausea and vomiting both. The composition is preferably administered in the form of a suppository. Again, the finely divided dexamethasone is not derived from a commercial dexamethasone tablet in this preferred embodiment. More preferably, the DEX is in the form of a micronized powder.

The clinical data is provided by the use and experience of a heterogeneous group of patients. Some have undergone, are undergoing, or will undergo chemotherapy. Still others are under the care of hospice groups. Most of these hospice group patients are terminally ill patients, including AIDS patients. Still other patients may have experienced a substantial or complete breakdown of their metabolic processes or capacity for metabolic function. Such breakdown may be the result of an advanced disease state, including but not limited to bacterial or viral infections one of whose pathological effects may be cell lysis, release of endogenous histamines and consequent inflammation.

The total number of patients reporting dramatic improvements in well being and/or substantial elimination of symptoms of nausea or emesis approaches about one to two hundred. As of the filing of the application, it is believed that the preferred composition has not failed to provide relief to a patient in need thereof. This knowledge alone, that a 100% effective anti-nausea, anti-emetic composition exists, is an invaluable tool that will allow the medical community to take a more aggressive stance in treating serious conditions and which will benefit patients in many unquantifiable ways, but mostly in the quality of their lives and the lives of those close to them. Furthermore, there is also a cost benefit to not having to continually look after and clean up after patients who have just vomited on themselves or their surroundings.

| Example | Dexamethasone (DEX) | Metoclopramide (MTC) | Diphenhydramine (DPH) | Reported Effectiveness |
|---|---|---|---|---|
| A |  |  |  |  |
| Roila | 20 mg iv | 3 mg/kg iv | 50 mg iv | 59% |
| B |  |  |  |  |
| Roila et al | 20 mg iv | 3 mg/kg 2 iv | 50 mg iv | 80.8% and 88.5% vomiting and nausea, first day, improves on days 2 & 3 |
| C |  |  |  |  |
| Warr et al | 10 mg iv | 2 mg/kg iv | 10 mg iv | 58% for emesis |
| D |  |  |  |  |
| Roila et al | 20 mg iv | 3 mg/kg iv | 50 mg iv | 58.1% vomiting high-dose cisplatin; 60.9% low dose |
| E |  |  |  |  |
| Francom | 10 mg | 40 mg | 25 mg | No data; suppository |
| F |  |  |  |  |
| Adamski | 5 mg | 20 mg | 25 mg | No data; suppository |
| G |  |  |  |  |
| Schmitt | 5 mg | 20 mg | 25 mg | 80% nausea and vomiting; rectal suppository |
| Naeger | 5 mg | 5 mg | 25 mg | 40-50% efficacy; suppository |
| Naeger | 10 mg | 10 mg | 25 mg | 60-80% efficacy |
| Naeger | 10 mg finely divided | 10 mg | 25 mg | 100% efficacy |

In addition to the compositions described above, the invention also contemplates other three- and four-component mixtures. These others include a preferred composition for pediatric use having about 5 mg of DEX, about 5 mg of MTC and about 12.5 mg of DPH. Still other embodiments may contain about 10 mg of DEX, about 20 mg of MTC and about 50 mg of DPH. For those patients who may experience some hyperactivity, the following embodiment may be used: about 5 mg DEX, about 10 mg MTC and about 25 mg DPH. Furthermore, a preferred four-component composition includes about 10 mg DEX, about 10 mg MTC, about 25 mg DPH and about 0.25 mg of SCP. Alternatively, a composition may use SCP in place of DPH altogether (e.g., about 10 mg DEX, about 10 mg MTC and about 0.25 mg SCP. The SCP may also replace the MTC entirely (e.g., about 10 mg DEX, about 25 mg DPH and about 0.25 mg SCP.

Only the preferred embodiment of the invention and but a few examples of its versatility are shown and described in the present disclosure. It is to be understood that the invention is capable of use in various other combinations and environments and is capable of changes or modifications within the scope of the inventive concept as expressed herein.

What is claimed is:

1. A pharmaceutical composition for the relief of nausea, emesis, or symptoms associated therewith comprising a combination of dexamethasone (DEX), metoclopramide (MTC), diphenhydramine (DPH) and an anticholinergic agent (ACA), said components DEX:MTC:DPH:ACA being present in a relative weight ratio of about 1:0–2:0–5:0–0.025, with the total weight of DEX, MTC and DPH in the composition ranging from 5 to 10 mgs, 5 to 20 mgs, and 12.5 to 50 mgs, respectively, provided that (i) the DEX is in the form of a micronized powder having a particle size in the range from about 5 µm to about 20 µm, (ii) no less than three of the four components are present and (iii) the composition does not include the combination DEX:MTC:DPH in a relative weight ratio of 1:1:5.

2. The composition of claim 1 in which the ACA is scopolamine (SCP).

3. The composition of claim 1 which comprises a combination of DEX:MTC:DPH in a relative weight ratio of about 0.9–1.1:0.9–1.1:2.0–3.0, respectively.

4. The composition of claim 1 which comprises a combination of DEX:MTC:DPH in a relative weight ratio of about 1:1:2.5, respectively.

5. The composition of claim 1 which comprises a combination of DEX:MTC:DPH:SCP as the ACA in a relative weight ratio of about 1:1:2.5:0.025, respectively.

6. The composition of claim 1 which comprises about 10 mg of DEX, about 10 mg of MTC and about 25 mg of DPH.

7. The composition of claim 1 in the form of a suppository.

8. The composition of claim 1 in which the DEX is a phosphate.

9. The composition of claim 8 in which the DEX is a dialkali metal salt of dexamethasone phosphate.

10. The composition of claim 1 in which the metoclopramide or diphenhydramine is present in the form of a free base or acid addition salt.

11. The composition of claim 1 in a form for parenteral administration.

12. A method of providing or maintaining relief from nausea, emesis and associated symptoms thereof comprising administering an effective amount of the composition of claim 1 to a patient in need thereof.

13. The method of claim 12 in which the patient is suffering from an emetogenic condition.

14. The method of claim 12 in which the patient is undergoing chemotherapy, about to undergo chemotherapy, or recovering from chemotherapy.

15. The method of claim 12 in which the patient is terminally ill.

16. The method of claim 12 in which the patient's metabolic functions have failed.

17. The method of claim 12 in which the patient is in the care of a hospice group.

18. The method of claim 12 in which the composition is administered chronically.

19. The method of claim 12 in which the composition is in the form of a controlled release formulation.

20. The method of claim 12 in which the composition is administered across a mucosal membrane of the patient.

21. A suppository for the relief of nausea, emesis, or symptoms associated therewith comprising a combination of dexamethasone (DEX), metoclopramide (MTC), diphenhydramine (DPH) and an anticholinergic agent (ACA), said components DEX:MTC:DPH:ACA being present in a relative weight ratio of about 1:0–2:0–5:0–0.025, with the total weight of DEX, MTC and DPH in the composition ranging from 5 to 10 mgs, 5 to 20 mgs, and 12.5 to 50 mgs, respectively, provided that (i) the DEX is in the form of a micronized powder having a particle size in the range from about 5 µm to about 20 µm, (ii) no less than three of the four components are present and (iii) the composition does not include the combination DEX:MTC:DPH in a relative weight ratio of 1:1:5.

22. The suppository of claim 21 in which the ACA is scopolamine (SCP).

23. The suppository of claim 21 which comprises about 10 mg of DEX, about 10 mg of MTC and about 25 mg of DPH.

* * * * *